US012672462B2

(12) United States Patent
Yang et al.

(10) Patent No.: US 12,672,462 B2
(45) Date of Patent: Jun. 30, 2026

(54) PPG SENSOR AND ELECTRONIC DEVICE

(71) Applicant: HUAWEI TECHNOLOGIES CO., LTD., Shenzhen (CN)

(72) Inventors: Sulin Yang, Dongguan (CN); Yapeng Li, Shenzhen (CN)

(73) Assignee: Huawei Technologies Co., LTD.

( * ) Notice: Subject to any disclaimer, the term of this patent is extended or adjusted under 35 U.S.C. 154(b) by 569 days.

(21) Appl. No.: 18/247,232

(22) PCT Filed: Sep. 2, 2021

(86) PCT No.: PCT/CN2021/116121
§ 371 (c)(1),
(2) Date: Mar. 29, 2023

(87) PCT Pub. No.: WO2022/068514
PCT Pub. Date: Apr. 7, 2022

(65) Prior Publication Data
US 2024/0008340 A1 Jan. 4, 2024

(30) Foreign Application Priority Data

Sep. 29, 2020 (CN) .......................... 202011050618.0

(51) Int. Cl.
*H10K 59/60* (2023.01)
*A61B 5/0205* (2006.01)
(Continued)

(52) U.S. Cl.
CPC ........... *H10K 59/60* (2023.02); *A61B 5/0205* (2013.01); *H10K 59/12* (2023.02); *H10K 59/353* (2023.02);
(Continued)

(58) Field of Classification Search
CPC . A61B 5/1455; A61B 5/14551; A61B 5/0205; A61B 5/02416; A61B 5/6897; A61B 5/6898
See application file for complete search history.

(56) References Cited

U.S. PATENT DOCUMENTS

2010/0164906 A1* 7/2010 Fukunaga ............. G06F 3/0412
345/175
2015/0346856 A1* 12/2015 Wassvik .................. G06F 3/042
345/175

FOREIGN PATENT DOCUMENTS

CN 211265482 U * 8/2020
WO WO-2017214582 A1 * 12/2017 ......... G06V 40/1318

* cited by examiner

*Primary Examiner* — Eric F Winakur
(74) *Attorney, Agent, or Firm* — Fish & Richardson P.C.

(57) ABSTRACT

An electronic device includes a body and a PPG sensor. The PPG sensor includes: a substrate, a first electrode, a light emitting layer, a light receiving layer, a second transparent electrode, and a transparent panel that are integrally packaged. The substrate and the first electrode are both located on one side of the light emitting layer, and the second transparent electrode and the transparent panel are both located on the other side of the light emitting layer. The light receiving layer, the first electrode, and the second transparent electrode are all located between the substrate and the transparent panel, and a polarity of the first electrode and a polarity of the second transparent electrode are opposite. The light emitting layer includes a light emitting pixel for emitting an optical signal, and the light receiving layer includes a light receiving pixel for detecting the optical signal.

20 Claims, 7 Drawing Sheets

(51) Int. Cl.
*A61B 5/1455*          (2006.01)
*H10K 59/12*           (2023.01)
*H10K 59/35*           (2023.01)
*H10K 59/40*           (2023.01)
*A61B 5/024*           (2006.01)

(52) U.S. Cl.
CPC .......... *H10K 59/40* (2023.02); *A61B 5/02416* (2013.01); *A61B 5/14551* (2013.01)

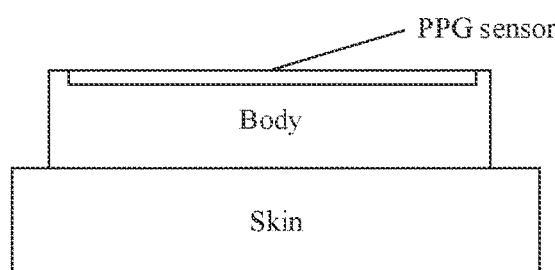
FIG. 5
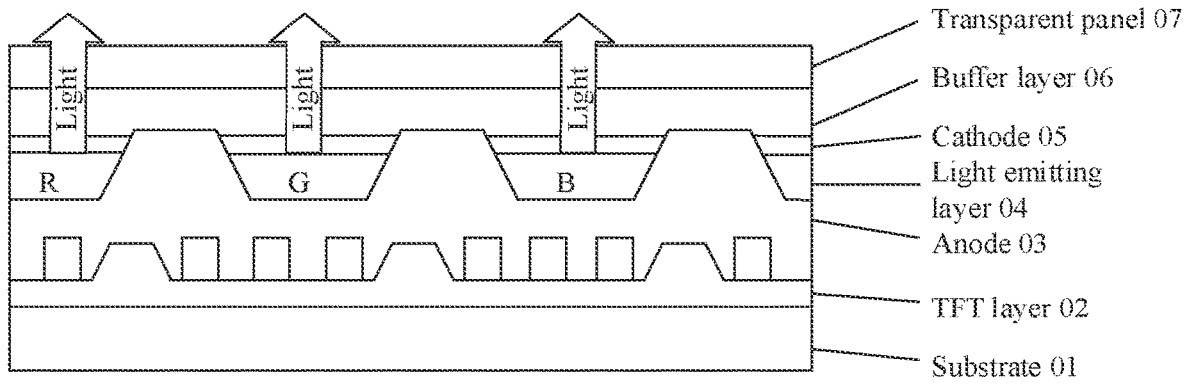
FIG. 6
| Transparent panel 07 |
| Buffer layer 06 |
| Cathode 05 |
| Light emitting layer 04 |
| Anode 03 |
| TFT layer 02 |
| Substrate 01 |
FIG. 7

(a)                    (b)

(c)

| Transparent panel 18 |
| Touch panel 17 |
| Polarizer 16 |
| Second transparent electrode 15 |
| Light emitting-receiving layer 14 |
| First electrode 13 |
| TFT layer 12 |
| Substrate 11 |

Transparent panel 18
Touch panel 17
Polarizer 16
Light receiving layer 142
Second transparent electrode 15
Light emitting layer 141
First electrode 13
TFT layer 12
Substrate 11

PPG SENSOR AND ELECTRONIC DEVICE

CROSS-REFERENCE TO RELATED APPLICATIONS

This application is a National Stage of International Application No. PCT/CN2021/116121, filed on Sep. 2, 2021, which claims priority to Chinese Patent Application No. 202011050618.0, filed on Sep. 29, 2020. Both of the aforementioned applications are hereby incorporated by reference in their entireties.

TECHNICAL FIELD

This application relates to the field of electronic technologies, and in particular, to a photoplethysmograph (PPG) sensor and an electronic device.

BACKGROUND

A PPG sensor is commonly used on smart wearable devices, such as a smartwatch and a smart band. Health data such as a heart rate and blood oxygen of a human body may be collected by using the sensor, to provide a basis for health analysis of the human body.

The PPG sensor mainly includes a light-emitting diode (LED) light source and a photodetector (PD). A detection principle of the PPG sensor is as follows: The LED emits optical signals. After the optical signals are transmitted to skin, some of the optical signals are absorbed by human tissue (including blood) in the skin, some of the optical signals are scattered and reflected, and some of the scattered and reflected optical signals are received by the PD and converted into electrical signals. The scattered and reflected optical signals regularly change with pulsation of pulses of a human body. A pulse wave change status can be detected based on a change of an electrical signal detected by the PD, so that data such as a heart rate and blood oxygen can be determined based on the pulse wave change status.

In a current PPG sensor, generally, an LED is packaged on an LED substrate, and then mounted on a printed circuit board (PCB) together with a PD. When a whole machine is assembled, a rear cover is assembled on the PCB to protect the LED and the PD. There is a safety gap between the rear cover and the LED. The PPG sensor with such a structure has high assembly costs and a large volume.

SUMMARY

In view of this, this application provides a PPG sensor and an electronic device, to reduce assembly costs and a volume of the PPG sensor.

To achieve the foregoing objective, according to a first aspect, an embodiment of this application provides a PPG sensor, including: a substrate, a first electrode, a light emitting layer, a light receiving layer, a second transparent electrode, and a transparent panel that are integrally packaged, where the substrate and the first electrode are both located on one side of the light emitting layer, and the second transparent electrode and the transparent panel are both located on the other side of the light emitting layer, and the light receiving layer, the first electrode, and the second transparent electrode are all located between the substrate and the transparent panel, and a polarity of the first electrode and a polarity of the second transparent electrode are opposite; and the light emitting layer includes a light emitting pixel for emitting an optical signal, and the light receiving layer includes a light receiving pixel for detecting the optical signal.

In the PPG sensor provided in this embodiment, the substrate, the first electrode, the light emitting layer including the light emitting pixel, the light receiving layer including the light receiving pixel, the second transparent electrode, and the transparent panel may be integrally packaged by using a display packaging process. In this way, assembly costs and a volume of the PPG sensor can be reduced, and a thickness of the PPG sensor and a gap between the PPG sensor and skin can be reduced.

In a possible implementation of the first aspect, the light emitting layer further includes display pixels arranged in an array.

In the foregoing implementation, the light emitting layer may further include the display pixels, that is, the PPG sensor and a display may be integrated together. In this way, an integration level of parts in an electronic device can be increased, so that a volume and a weight of the electronic device can be reduced.

In a possible implementation of the first aspect, the light emitting layer and the light receiving layer are integrated in a same light emitting-receiving layer. In this way, a thickness of the PPG sensor can be reduced to a specific extent.

In a possible implementation of the first aspect, the light emitting layer includes a central region and an edge region around the central region, the display pixels are distributed in the central region, and the light emitting pixel and the light receiving pixel are distributed in the edge region. This facilitates manufacturing of the PPG sensor.

In a possible implementation of the first aspect, the display pixels include a first display pixel, a second display pixel, and a third display pixel in different colors, and three colors of the first display pixel, the second display pixel, and the third display pixel are respectively red, green, and blue; and the first display pixel and target pixels are alternately arranged in a first direction, the first display pixel and the second display pixel are alternately arranged in a second direction, the second display pixel and the third display pixel are alternately arranged in the first direction, and the first direction is perpendicular to the second direction; and there are a plurality of light emitting pixels and a plurality of light receiving pixels, and the target pixels include at least some of the light emitting pixels and at least some of the light receiving pixels.

In the implementation, the display pixels and the target pixels corresponding to the PPG sensor are alternately arranged. In this way, the target pixels are relatively evenly distributed, so that a signal collection effect can be improved.

In a possible implementation of the first aspect, the light emitting pixels relate to a plurality of wavelengths, the target pixels include all the light emitting pixels and all the light receiving pixels, and all target pixels adjacent to the light receiving pixels are the light emitting pixels. In this way, the light emitting pixels with different wavelengths may send optical signals with different wavelengths, and correspondingly, the light receiving pixels may collect optical signals with a plurality of wavelengths, so that a more accurate detection result can be obtained during PPG detection. Moreover, all target pixels adjacent to the light receiving pixels are the light emitting pixels. In this way, a light receiving effect of the light receiving pixel can be improved.

In a possible implementation of the first aspect, for each light receiving pixel, light emitting pixels adjacent to the light receiving pixel include a red light emitting pixel and an infrared light emitting pixel, a distance between the red light emitting pixel and the light receiving pixel is equal to a distance between the infrared light emitting pixel and the light receiving pixel. In this way, accuracy of a blood oxygen detection result can be enhanced during blood oxygen detection.

In a possible implementation of the first aspect, the light emitting pixels include a first light emitting pixel, a second light emitting pixel, and a green light emitting pixel, one of the first light emitting pixel and the second light emitting pixel is the red light emitting pixel, and the other is the infrared light emitting pixel; and the first light emitting pixel and the green light emitting pixel are alternately arranged in the first direction, the first light emitting pixel and the light receiving pixel are alternately arranged in the second direction, and the light receiving pixel and the second light emitting pixel are alternately arranged in the first direction.

In a possible implementation of the first aspect, the light emitting pixels include at least some red display pixels and/or at least some green display pixels among the display pixels, and the target pixels include the light receiving pixels.

In the implementation, the light emitting pixels and the display pixels share the red and/or green display pixels. In this way, pixel utilization can be increased, and manufacturing complexity of the PPG sensor can be reduced.

In a possible implementation of the first aspect, the light emitting pixels further include infrared light emitting pixels, and the target pixels further include the infrared light emitting pixels; and all target pixels adjacent to the light receiving pixels are the infrared light emitting pixels, and/or all target pixels adjacent to the infrared light emitting pixels are the light receiving pixels. In this way, a light receiving effect of the light receiving pixel can be improved.

In a possible implementation of the first aspect, each display pixel includes four subpixels in corresponding colors. In this way, a quantity of pixels in a unit area can be increased, so that display resolution can be increased.

In a possible implementation of the first aspect, the display pixels include red display pixels, green display pixels, and blue display pixels, the light emitting layer includes pixel units arranged in an array, each pixel unit includes one red display pixel, one green display pixel, one blue display pixel, and one target pixel that are sequentially arranged in a first direction, there are a plurality of light emitting pixels, and the target pixels include at least some of the light emitting pixels.

In a possible implementation of the first aspect, the light emitting pixels include an infrared light emitting pixel, a red light emitting pixel, and a green light emitting pixel, and the target pixels include all the light emitting pixels; or the light emitting pixels include at least some red display pixels and at least some green display pixels among the display pixels, and an infrared light emitting pixel, and the target pixels include the infrared light emitting pixel.

In a possible implementation of the first aspect, the light emitting layer and the light receiving layer are integrated in a same light emitting-receiving layer, and the target pixels further include the light receiving pixel. In this way, a thickness of the PPG sensor can be reduced to a specific extent.

In a possible implementation of the first aspect, there is an isolation column between the display pixel and each adjacent pixel among the target pixels, the light receiving pixel is disposed on the isolation column, and each light receiving pixel forms one light receiving layer. In this way, space utilization can be increased, and a thickness of the PPG sensor can be reduced.

In a possible implementation of the first aspect, a light source of the display pixels is a miniature light-emitting diode LED, and a light source of the light emitting pixel is a miniature LED or a vertical-cavity surface-emitting laser VCSEL. In this way, a miniature PPG sensor can be implemented, so that an application scope of the PPG sensor can be expanded.

In a possible implementation of the first aspect, there are a plurality of light emitting pixels and a plurality of light receiving pixels, the light emitting pixels relate to a plurality of wavelengths, the light emitting layer and the light receiving layer are integrated in a same light emitting-receiving layer, and the light emitting pixels with various wavelengths and the light receiving pixels are alternately arranged.

In a possible implementation of the first aspect, each pixel adjacent to the light receiving pixel is a light emitting pixel. In this way, a light receiving effect of the light receiving pixel can be improved.

In a possible implementation of the first aspect, the light receiving layer is located between the second transparent electrode and the transparent panel.

In a possible implementation of the first aspect, the electronic device further includes a thin film transistor TFT layer located between the substrate and the first electrode, and a drive circuit of the light emitting pixel and a receiver circuit of the light receiving pixel are integrated in the TFT layer. In this way, assembly costs and a volume of the PPG sensor can be further reduced.

In a possible implementation of the first aspect, an analog front end AFE circuit is integrated in the TFT layer, and the AFE is configured to amplify and sample an optical signal received by the receiver circuit. In this way, assembly costs and a volume of the PPG sensor can be further reduced.

In a possible implementation of the first aspect, the PPG sensor further includes a polarizer and/or a touch panel that are/is located between the second transparent electrode and the transparent panel. Reflected light can be absorbed by using the polarizer, to reduce reflection interference from external light and enhance contrast. The touch panel can enable the PPG sensor to implement a touch detection function.

According to a second aspect, an embodiment of this application provides an electronic device, including a body and the PPG sensor according to the first aspect, where the PPG sensor is disposed on the body and is electrically connected to a circuit board in the body.

It can be understood that, for beneficial effects of the second aspect, refer to the related descriptions in the first aspect. Details are not described herein again.

BRIEF DESCRIPTION OF DRAWINGS

FIG. 5 is a schematic diagram of still another application scenario according to an embodiment of this application;

FIG. 6 is a schematic diagram of a structure of an OLED display according to an embodiment of this application;

FIG. 7 is a schematic diagram of a relationship between packaging layers in FIG. 6;

DESCRIPTION OF EMBODIMENTS

The following describes the embodiments of this application with reference to the accompanying drawings in the embodiments of this application. Terms used in the implementations of the embodiments of this application are merely intended to describe specific embodiments of this application, but not to limit this application.

Figure 1:
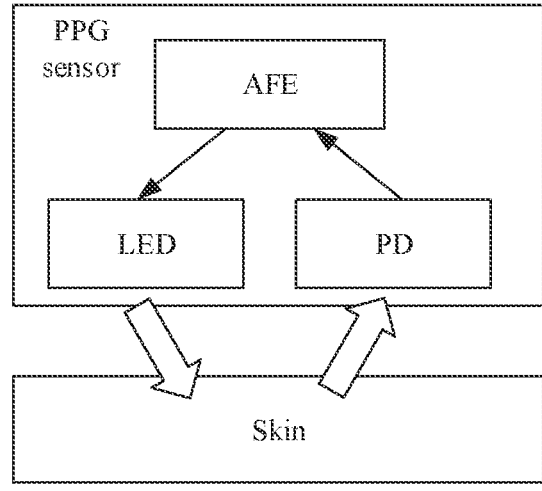
FIG. 1 is a schematic diagram of a working principle of an existing PPG sensor.

Currently, PPG sensors are often used on smart wearable devices to measure physiological data, such as a heart rate and blood oxygen. FIG. 1 is a schematic diagram of a working principle of an existing PPG sensor. As shown in FIG. 1, the PPG sensor mainly includes an LED and a PD. For ease of control, the PPG sensor may further include an analog front end (AFE) circuit. The PD may be a photodetector device such as a photodiode or a phototransistor.

During working, the AFE may drive the LED to emit optical signals. After the optical signals are transmitted to skin, some of the optical signals are absorbed by human tissue (including blood) in the skin, the other optical signals are scattered and reflected, and some of the scattered and reflected optical signals are received by the PD and converted into electrical signals. After receiving the electrical signal output by the PD, the AFE may amplify and sample the electrical signal, to obtain a pulse wave signal.

Heart beats of a human body are transferred to skin capillaries through blood vessels, causing a blood volume to change. When a heart contracts, the blood vessels expand, the blood volume increases, more optical signals are absorbed, and scattered signals decrease. When the heart relaxes, the blood vessels recover, the blood volume recovers, the absorbed optical signals decrease, and the scattered signals increase. Therefore, the scattered and reflected optical signals regularly change with pulsation of pulses of the human body. A pulse wave change status can be detected based on a change of an electrical signal detected by the PD, so that data such as a heart rate and blood oxygen can be determined based on the pulse wave change status.

Figure 2:
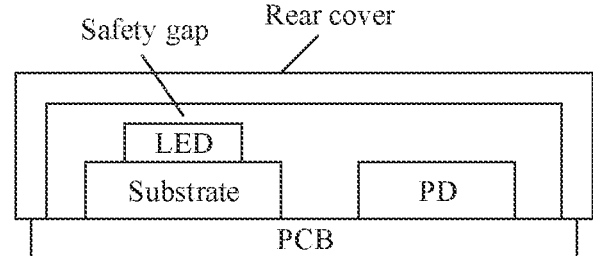
FIG. 2 is a schematic diagram of a structure of an existing PPG sensor.

A structure of a current packaged PPG sensor is generally shown in FIG. 2. The LED is packaged on a substrate, the packaged LED and PD are mounted on a PCB, and when a whole machine is assembled, a rear cover is assembled on the PCB to protect the LED and the PD. There is a safety gap between the rear cover and the LED.

The PPG sensor with this structure has separate parts and many assembling processes, leading to high assembling costs. In addition, a PPG has a relatively large overall volume and thickness (a thickness of the PCB+a thickness of the LED substrate+a thickness of the LED+the safety gap+a thickness of the rear cover), and a gap between the LED and skin and a gap between the PD and the skin are excessively large. This is not conducive to PPG detection.

To resolve the foregoing technical problem, the embodiments of this application provide a PPG sensor and an electronic device. The PPG sensor is mainly implemented by using an organic light-emitting diode (OLED) display process, to reduce assembly costs and a volume of the PPG sensor, and reduce a thickness of the PPG sensor and a gap between the PPG sensor and skin.

The PPG sensor provided in this embodiment of this application may be applied to a smart wearable device. The smart wearable device may be a wearable device that can support health monitoring of a human body, such as a smartwatch, a smart band, or a smart eye mask. It can be understood that the PPG sensor provided in this embodiment of this application may also be used on an electronic device, such as a mobile phone, a tablet computer, or a computer. This is not particularly limited in this embodiment of this application. For ease of understanding, several application scenarios of the PPG sensor are described below by using a smartwatch as an example.

Figure 3:
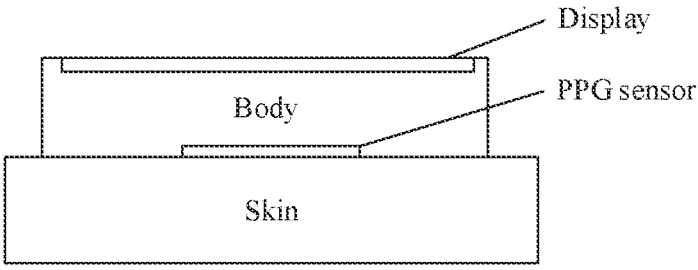
FIG. 3 is a schematic diagram of an application scenario according to an embodiment of this application.

In a first application scenario, FIG. 3 is a schematic diagram of an application scenario according to an embodiment of this application. As shown in FIG. 3, a display is disposed on a front side of a body of the smartwatch, and the PPG sensor may be disposed on a rear side of the body of the smartwatch, and directly comes into contact with skin.

In practical application, the PPG sensor may be controlled to implement continuous and imperceptible PPG detection. Certainly, a working state of the PPG sensor may also be controlled by using an enabled/disabled state of a PPG detection function. For example, a user may enable the PPG detection function by using a related health management application. Correspondingly, when the PPG detection function is enabled, the PPG sensor may be started to perform PPG detection. When it is detected that the user disables the PPG detection function, or after preset detection duration, the PPG sensor is controlled to stop PPG detection.

Figure 4:
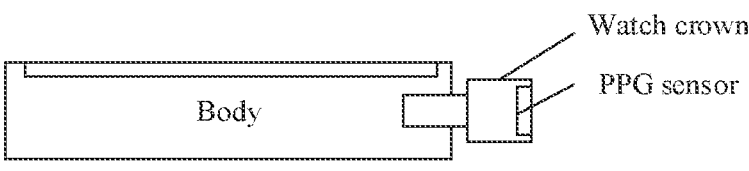
FIG. 4 is a schematic diagram of another application scenario according to an embodiment of this application.

In a second application scenario, FIG. 4 is a schematic diagram of another application scenario according to an embodiment of this application. As shown in FIG. 4, the PPG sensor may be disposed on a side surface of a body of the smartwatch. For example, when a watch crown is disposed on the side surface of the body, the PPG sensor may be disposed on the side surface of the watch crown.

During PPG detection, a user may come into contact with the PPG sensor by using a finger or skin of another part of a human body, to measure a pulse wave signal.

In a third application scenario, FIG. 5 is a schematic diagram of still another application scenario according to an embodiment of this application. As shown in FIG. 5, the PPG sensor and a display may be integrated together, and are disposed on a front side of a body of the smartwatch.

During PPG detection, a user may come into contact with the PPG sensor by using a finger or skin of another part of a human body, to measure a pulse wave signal. When the smartwatch normally works, the PPG sensor may be used for displaying. During PPG detection, displaying may be stopped to perform PPG detection, or displaying and PPG detection may be simultaneously performed, or displaying and PPG detection may be separately performed, that is, displaying and PPG detection may be alternately performed.

Similar to a connection manner between the display and a circuit board that are on the body, the PPG sensor may be electrically connected to the circuit board (not shown) of the body directly or indirectly, to communicate with a processor on the circuit board, to implement the PPG detection function and a display function. For example, the PPG sensor may be soldered on the circuit board, or may be connected to the circuit board by using some connection wires and connection interfaces. During specific implementation, selection may be performed as required. This is not particularly limited in this embodiment.

As described above, in this embodiment of this application, the PPG sensor is implemented by using an OLED display packaging process. For ease of understanding, the following first describes an OLED display.

FIG. 6 is a schematic diagram of a structure of an OLED display according to an embodiment of this application. FIG. 7 is a schematic diagram of a relationship between packaging layers in FIG. 6. As shown in FIG. 6 and FIG. 7, the OLED display may include a substrate 01, an anode 03, a light emitting layer 04, a cathode 05, and a transparent panel 07 that are sequentially disposed from bottom to top.

A light emitting principle of the OLED display is as follows: When there is a forward bias voltage, the cathode 05 generates an electron, the anode 03 generates an electron hole, the electron and the electron hole are transmitted to the light emitting layer 04 under the action of field stress, and then recombined in the light emitting layer 04, thereby exciting a molecule of the light emitting layer to generate a singlet exciton. Radiation of the singlet exciton attenuates to emit light.

The substrate 01 may play a supporting role, and the substrate 01 may be made of a glass or plastic material. The transparent panel 07 mainly plays a role in protecting the entire display. A material of the transparent panel 07 is usually glass. Certainly, the transparent panel 07 may alternatively be made of another material, provided that the material is transparent and has specific strength.

The cathode 05 and the anode 03 may be formed by using an evaporation process, and locations of the cathode 05 and the anode 03 may be interchanged, and an electrode near the transparent panel 07 is a transparent electrode, to facilitate light transmission. The OLED display may perform top light emitting and bottom light emitting. When bottom light emitting is performed, each layer at the bottom of the light emitting layer 04 is of a transparent structure. In FIG. 6, an example of top light emitting is used for description.

The light emitting layer 04 is composed of organic material molecules, and a pixel array in the light emitting layer 04 may be formed by using a process such as evaporation or ink jet printing. Each pixel may emit light under the driving of the driving circuit, and light intensity of the pixel may be adjusted by controlling magnitude of a current.

In a pixel driving manner, the OLED display may be classified into a passive matrix organic light-emitting diode (PMOLED) and an active matrix organic light-emitting diode (AMOLED).

The PMOLED includes a matrix of a cathode strip and an anode strip that are perpendicular to each other, a pixel is formed at a cross point of the cathode strip and the anode strip, and a current is exerted to a selected cathode strip and a selected anode strip by using an external drive circuit to light up the pixel in the array.

In the AMOLED, a thin film transistor (TFT) layer is formed between the substrate 01 and the electrode, to drive a pixel. In this manner, driving precision is relatively high. In FIG. 6 and FIG. 7, examples of the AMOLED are used for description. As shown in FIG. 6 and FIG. 7, a TFT layer 02 is formed between the substrate 01 and the anode 03, and the TFT layer 02 is controlled to control each pixel in the light emitting layer 04 to work, to generate a corresponding image. The TFT layer 02 may be formed by using film formation, exposure, and etching processes.

As shown in FIG. 6, a buffer layer 06 may be further formed between the transparent panel 07 and the cathode 05 to serve as a connection or the like. For example, a polarizer may be added between the transparent panel 07 and the cathode 05 to absorb reflected light, thereby reducing reflection interference from external light, and enhancing contrast. The polarizer may be located in the buffer layer 06.

Figures 8, 9:
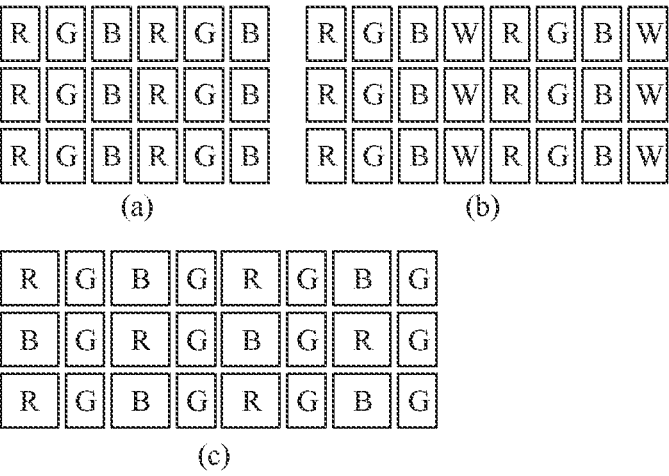
FIG. 8 is a schematic diagram of an arrangement structure of pixels of an OLED display according to an embodiment of this application.
FIG. 9 is a schematic diagram of a relationship between packaging layers of a PPG sensor according to an embodiment of this application.

Pixels in the light emitting layer 04 may be in different colors. FIG. 6 shows an example of one red (R) pixel, one green (G) pixel, and one blue (B) pixel. The pixels may be arranged according to a rule. FIG. 8 is a schematic diagram of an arrangement structure of pixels of an OLED display according to an embodiment of this application. As shown in FIG. 8, pixel arrangement manners of pixel arrays in the light emitting layer 04 may include the following several types:

First: RGB arrangement. As shown in (a) in FIG. 8, the R pixel, the G pixel, and the B pixel are arranged side by side to form one pixel unit, and pixel units are arranged repeatedly in a row direction and in a column direction to form a pixel array. In FIG. 6, a pixel structure of one pixel unit is shown by using RGB arrangement as an example.

Second: RGBW arrangement. As shown in (b) in FIG. 8, in the RGBW arrangement manner, in addition to the original RGB pixels, a white (W) pixel is added.

Third: Pentile arrangement. As shown in (c) in FIG. 8, each pixel unit in the Pentile arrangement includes RG or BG. During displaying, each pixel unit and a pixel adjacent to the pixel unit share a red pixel or a blue pixel.

It can be understood that the foregoing merely enumerates three common pixel arrangement manners, and the light emitting layer 04 may also use another pixel arrangement manner, such as honeycomb arrangement and diamond arrangement. This is not particularly limited in this embodiment.

A structure of the PPG sensor is described below.

FIG. 9 is a schematic diagram of a relationship between packaging layers of a PPG sensor according to an embodiment of this application. As shown in FIG. 9, the PPG sensor includes a substrate 11, a first electrode 13, a light emitting-receiving layer 14, a second transparent electrode 15, and a transparent panel 18 that are integrally packaged. The substrate 11 and the first electrode 13 are both located on one side of the light emitting-receiving layer 14, and the second transparent electrode 15 and the transparent panel 18 are both located on the other side of the light emitting-receiving layer 14. The first electrode 13 and the second transparent electrode 15 are both located between the substrate 11 and the transparent panel 18, and a polarity of the first electrode 13 and a polarity of the second transparent electrode 15 are opposite. The light emitting-receiving layer 14 includes a light emitting pixel for emitting an optical signal and a light receiving pixel for detecting the optical signal.

It can be understood that the light emitting pixel and the light receiving pixel may also be located in different layers, that is, the light emitting pixel is located in a light emitting layer, the light receiving pixel is located in a light receiving layer, and the light emitting layer and the light receiving layer are separately disposed. In FIG. 9, an example in which the light emitting layer and the light receiving layer are integrated in the same light emitting-receiving layer 14 is used for description.

Specifically, structures and functions of the substrate 11 and the transparent panel 18 are similar to those of the substrate 11 and the transparent panel 18 in the OLED display. Details are not described herein again.

The first electrode 13 may be an anode or a cathode, and correspondingly, the second transparent electrode 15 may be a cathode or an anode. The first electrode 13 may be a transparent or non-transparent material.

The light emitting-receiving layer 14 may be formed by using organic material molecules. A specific material is not specifically limited in this application. The light emitting pixel and the light receiving pixel in the light emitting-receiving layer 14 may also be formed by using an evaporation process or another process. A light source of the light emitting pixel may be an LED, a micro LED, a vertical-cavity surface-emitting laser (VCSEL), or the like, and the light receiving pixel may be a PD device or a PD chip.

As shown in FIG. 9, a polarizer 16 may be disposed between the second transparent electrode 15 and the transparent panel 18, to absorb reflected light, thereby reducing reflection interference from external light, and enhancing contrast. The polarizer 16 may alternatively be replaced with a light filter or an array filter, to filter out an optical signal of an irrelevant wavelength, thereby improving signal contrast or signal quality. For example, in a PD that is responsible for receiving only red light, a location corresponding to the array filter is a wavelength for transmitting red light, and no light of another wavelength can be transmitted.

A touch panel 17 may also be disposed between the second transparent electrode 15 and the transparent panel 18, to serve as a triggering condition for a touch input or for starting PPG detection. For example, PPG detection may be started when a touch operation of a user is detected. Alternatively, when it is detected that a continuous touch time of a user exceeds preset duration, PPG detection is started. Alternatively, when a PPG detection function is enabled, when a touch operation of a user is detected, PPG detection is started. A specific PPG detection starting manner may be selected as required. This is not particularly limited in this embodiment.

When the PPG sensor is used on a rear side of a smartwatch, the touch panel 17 may be a capacitive sensor, and is used to detect wearing. When skin comes into contact with the PPG sensor, it may be detected that the smartwatch is in a worn state. In this case, PPG detection may be performed. Specifically, an occasion for starting PPG detection is similar to that described above, and PPG detection may be started when it is detected that the smartwatch is in the worn state. Alternatively, when the PPG detection function is enabled, PPG detection may be started when it is determined that the smartwatch is in the worn state. A specific PPG detection starting manner is not particularly limited in this embodiment.

When the polarizer 16 and the touch panel 17 are both disposed between the second transparent electrode 15 and the transparent panel 18, the polarizer 16 may be located between the touch panel 17 and the transparent panel 18, or the touch panel 17 may be located between the polarizer 16 and the transparent panel 18. Specifically, selection may be performed as required. In FIG. 9, that the touch panel 17 is located between the polarizer 16 and the transparent panel 18 is merely used as an example for description, rather than a limitation on this application.

To expand an application range, the light emitting-receiving layer 14 may further include display pixels arranged in an array, that is, the PPG sensor and the OLED display may be integrated together. It can be understood that, when the PPG sensor is not used on a front side of the smartwatch, no display pixel may be disposed, to reduce costs.

The following separately describes a pixel arrangement structure for a case in which the PPG sensor includes display pixels and a pixel arrangement structure for a case in which the PPG sensor includes no display pixel.

(1) A Case in which the PPG Sensor Includes Display Pixels.

When pixels are formed, a light emitting pixel and a light receiving pixel may be disposed around a display pixel array, that is, the light emitting-receiving layer 14 may include a central region and an edge region around the central region, the display pixels are distributed in the central region, and the light emitting pixel and light receiving pixel are distributed in the edge region. The pixel arrangement manner of display pixels may be RGB arrangement, RGBW arrangement, Pentile arrangement, or the like. There may be one or more light emitting pixels and one or more light receiving pixels. Specific quantities are not particularly limited in this embodiment.

Alternatively, light emitting pixels or light receiving pixels may be disposed at some pixel locations of the display pixel array. The light emitting pixels, the light receiving pixels, and the display pixels may be arranged irregularly or according to a rule, to improve a display effect and a PPG detection effect.

Figure 10:
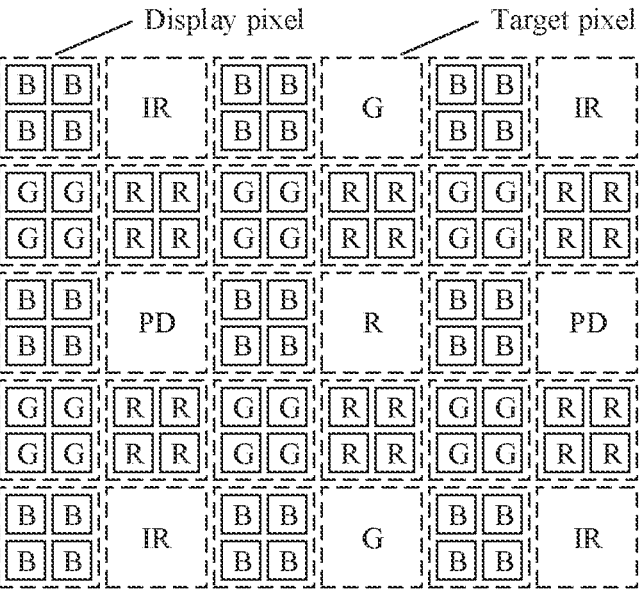
FIG. 10 is a schematic diagram of an arrangement structure of pixels according to an embodiment of this application.

FIG. 10 is a schematic diagram of an arrangement structure of pixels according to an embodiment of this application. As shown in FIG. 10, display pixels include a first display pixel, a second display pixel, and a third display pixel in different colors, and three colors of the first display pixel, the second display pixel, and the third display pixel are respectively red, green, and blue.

The first display pixel and target pixels are alternately arranged in a first direction, the first display pixel and the second display pixel are alternately arranged in a second direction, the second display pixel and the third display pixel are alternately arranged in the first direction, and the first direction is perpendicular to the second direction. There may be a plurality of light emitting pixels and a plurality of light receiving pixels, and the target pixels include the light emitting pixels and the light receiving pixels.

It should be noted that, in FIG. 10, that the first display pixel is a B display pixel, the second display pixel is a G display pixel, the third display pixel is an R display pixel, and the first direction is a row direction is used as an example for description, rather than a limitation on this application. During specific implementation, locations of the R display pixel, the G display pixel, and the B display pixel may be interchanged, and the first direction may alternatively be a column direction.

During displaying, a first display pixel, a second display pixel, and a third display pixel that are adjacent may be used as one pixel unit. Light intensity of each of the first display pixel, the second display pixel, and the third display pixel is controlled, so that the pixel unit may emit light in different colors.

To increase display resolution, in this embodiment, each display pixel may include four subpixels in corresponding colors. For example, the R display pixel in the figure includes four R subpixels, the G display pixel includes four G subpixels, and the B display pixel includes four B subpixels. These subpixels are represented by using solid-line square boxes, the letters R, G. and B in the boxes represent colors of the corresponding subpixels, and a dashed square box outside the solid-line square boxes represents a corresponding display pixel. During displaying, the R subpixel, the G subpixel, and the B subpixel that are adjacent may be used as one pixel unit. In this way, a quantity of pixels in a unit area can be increased, so that display resolution can be increased.

In this embodiment, the light emitting pixels may relate to a plurality of wavelengths. As shown in FIG. 10, the light emitting pixels may include an R light emitting pixel, a G light emitting pixel, and an infrared (IR) light emitting pixel. These light emitting pixels and the light receiving pixels are represented by using dashed square boxes that include no solid-line square box, the letters R, G, and IR in the boxes represent types of corresponding light emitting pixels, and PD represents a light receiving pixel. Each light receiving pixel PD may receive optical signals of one or more wavelengths.

It can be understood that, the light emitting pixels may include one or more of the R light emitting pixel, the G light emitting pixel, and the IR light emitting pixel, and the wavelengths related to the light emitting pixels may also include another wavelength. This is not particularly limited in this embodiment. Each light emitting pixel may also include a plurality (for example, four) of subpixels with corresponding wavelengths. Selection may be performed as required during specific implementation.

When the light emitting pixels and the light receiving pixels are arranged, the light emitting pixels and the light receiving pixels may be arranged irregularly or according to a rule, to improve a PPG detection effect. As shown in FIG. 10, target pixels adjacent to the light receiving pixels may all be light emitting pixels, so that a light receiving effect of the light receiving pixel can be improved.

To enhance accuracy of a blood oxygen detection result, for an R light emitting pixel, an IR light emitting pixel, and a PD light receiving pixel that are adjacent, a distance between the R light emitting pixel and the PD light receiving pixel is equal to a distance between the IR light emitting pixel and the light receiving pixel PD.

During specific implementation, the R light emitting pixel and the IR light emitting pixel may be located in a row direction or a column direction of the light receiving pixel PD, or may be located in four diagonal corners of a square centered on the light receiving pixel PD.

In an optional implementation, when the light emitting pixels include the G light emitting pixel, a location relationship among the R light emitting pixel, the G light emitting pixel, the IR light emitting pixel, and the light receiving pixel may be shown in FIG. 10. The first light emitting pixel and the G light emitting pixel are alternately arranged in a first direction, the first light emitting pixel and the light receiving pixel are alternately arranged in a second direction, and the light receiving pixel and the second light emitting pixel are alternately arranged in the first direction. One of the first light emitting pixel and the second light emitting pixel is an R light emitting pixel and the other is an IR light emitting pixel.

Figure 11:
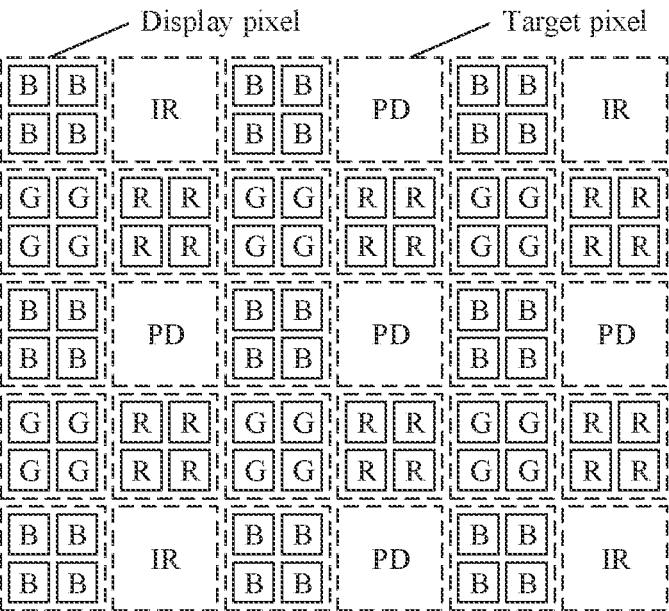
FIG. 11 is a schematic diagram of another arrangement structure of pixels according to an embodiment of this application.

FIG. 11 is a schematic diagram of another arrangement structure of pixels according to an embodiment of this application. As shown in FIG. 11, to increase pixel utilization, in this embodiment of this application, light emitting pixels may share an R pixel and a G pixel with display pixels. All or some of R display pixels and G display pixels among the display pixels may be used as shared pixels, that is, the light emitting pixels may include at least some of the R display pixels and at least some of the G display pixels among the display pixels. Target pixels may include a light receiving pixel, the light emitting pixels may further include another pixel, and the target pixels may also include the another pixel. For example, the light emitting pixels include an IR light emitting pixel, and the target pixels may also include the IR light emitting pixel.

A structure of the display pixels and an arrangement relationship between the display pixels and the target pixels are similar to those in FIG. 10. Details are not described herein again.

When the light emitting pixels and the light receiving pixels are arranged, the light emitting pixels and the light receiving pixels may be arranged irregularly or according to a rule, to improve a PPG detection effect. As shown in FIG. 11, when the target pixels include an IR light emitting pixel, all target pixels adjacent to a light receiving pixel PD may be IR light emitting pixels, and all target pixels adjacent to the IR light emitting pixel may be light receiving pixels PD. In this way, a light receiving effect of the light receiving pixel can be improved.

It can be understood that, w % ben the light emitting pixels include no IR light emitting pixel, the target pixels may all be light receiving pixels PD. The light emitting pixels and the display pixels may share one or more of the R pixels, the G pixel, and B pixels. In this embodiment, that the light emitting pixels and the display pixels share the R pixel and the G pixel is only used as example for description.

Figure 12:
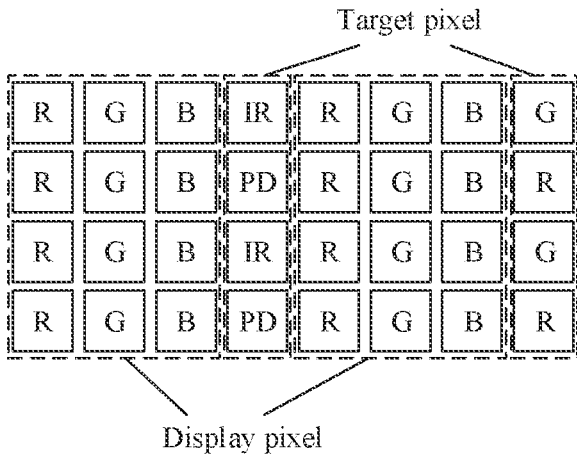
FIG. 12 is a schematic diagram of still another arrangement structure of pixels according to an embodiment of this application.
Figure 13:
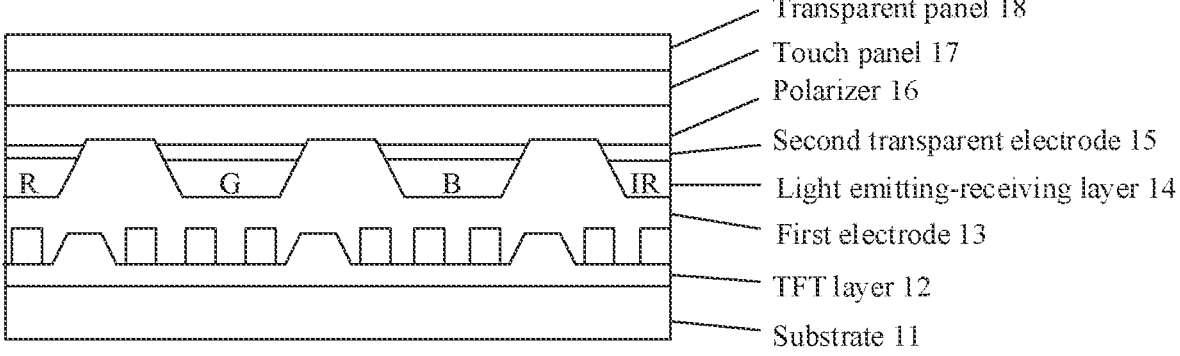
FIG. 13 is a schematic diagram of a structure of a PPG sensor corresponding to FIG. 12.

FIG. 12 is a schematic diagram of still another arrangement structure of pixels according to an embodiment of this application. FIG. 13 is a schematic diagram of a structure of a PPG sensor corresponding to FIG. 12. As shown in FIG. 12 and FIG. 13, display pixels include R display pixels, G display pixels, and B display pixels, a light emitting-receiving layer 14 includes pixel units arranged in an array, each pixel unit includes one R display pixel, one G display pixel, one B display pixel, and one target pixel that are sequentially arranged in a first direction, there are a plurality of light emitting pixels and a plurality of light receiving pixels, and target pixels may include at least some of the light emitting pixels and at least some of the light receiving pixels.

When the first direction is a row direction, a pixel unit may be correspondingly of a four-column pixel structure. When the first direction is a column direction, the pixel unit may be correspondingly of a four-row pixel structure, that is, display pixels in each pixel unit may use a three-row or three-column RGB arrangement manner, and a light emitting pixel and a light receiving pixel may be correspondingly disposed as a fourth row or a fourth column. In the figure, an example in which the first direction is a row direction is used for description. This is not used to limit this application.

The display pixels may also include another pixel, for example, a W display pixel. Correspondingly, the pixel unit may also include the W display pixel, and the W display pixel may be located after the B display pixel, that is, the display pixels in each pixel unit may use a four-row or four-column RGBW arrangement manner. A light emitting pixel and a light receiving pixel may be correspondingly disposed as a fifth row or a fifth column.

Similar to the pixel arrangement manner shown in FIG. 10, the light emitting pixels may share no pixel with the display pixels, that is, the target pixels may include each light emitting pixel and each light receiving pixel. The light emitting pixels may include an IR light emitting pixel, an R light emitting pixel, and a G light emitting pixel. Certainly, the light emitting pixels may also include a pixel with another wavelength. This may be specifically selected as required.

Similarly, similar to the pixel arrangement manner shown in FIG. 11, the light emitting pixels may alternatively share a pixel with the display pixels, that is, the light emitting pixels may include at least some R display pixels and at least some G display pixels among the display pixels. The target pixels may include a light receiving pixel, the light emitting pixels may further include another pixel, the target pixels may also include the another pixel. For example, the light emitting pixels include an IR light emitting pixel, and the target pixels may also include the IR light emitting pixel. In FIG. 13, an example of a pixel unit including an IR light emitting pixel is used for description.

An arrangement relationship between the light emitting pixels and the light receiving pixels is similar to the pixel arrangement manners shown in FIG. 10 and FIG. 11. Arrangement may be performed irregularly or according to a rule, to improve a PPG detection effect. For a specific arrangement manner, refer to related descriptions of the pixel arrangement manners shown in FIG. 10 and FIG. 11. Details are not described herein again.

Figure 14:
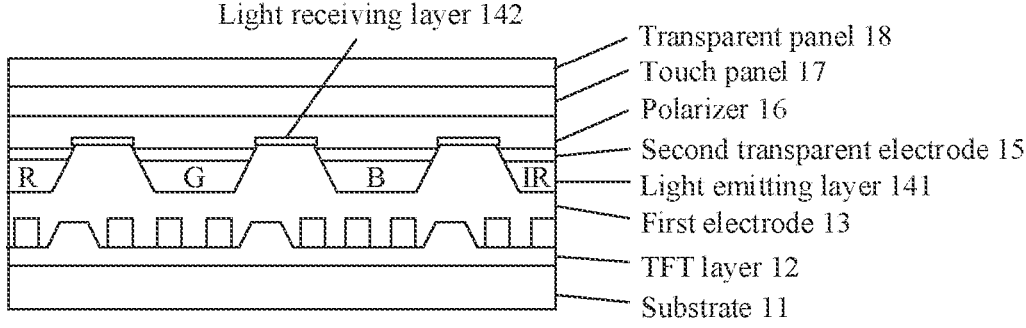
FIG. 14 is a schematic diagram of another structure of a PPG sensor according to an embodiment of this application.

As described above, a light emitting layer 141 and a light receiving layer 142 may alternatively be separately disposed. Correspondingly, both the display pixel and the light emitting pixel may be located in the light emitting layer 141, and the light receiving pixel PD may be located in the light receiving layer 142. FIG. 14 is a schematic diagram of a location of a light receiving pixel according to an embodiment of this application. As shown in FIG. 14, there is an isolation column between a display pixel and each adjacent pixel among the target pixels, the light receiving pixel may be disposed on the isolation column, and each light receiving pixel forms one light receiving layer 142.

The isolation column may be an insulating material, and is used to separate different pixels, to implement a pixel array. The light receiving pixel may be disposed at the top of the isolation column. There may be one or more light receiving pixels, and a specific quantity may be selected as required. When a plurality of light receiving pixels are included, the light receiving pixels may be evenly distributed on isolation columns, and the light receiving pixels disposed on the isolation columns form a plurality of light receiving layers 142 distributed at intervals.

A location relationship between the light emitting pixel and the display pixel may be consistent with the location relationship between the light emitting pixel and the display pixel in the implementation shown in FIG. 10, FIG. 11, or FIG. 12. It can be understood that, when the location relationship between the light emitting pixel and the display pixel in the pixel arrangement manner shown in FIG. 12 is used, when the light emitting pixel includes only the shared pixel, the pixel unit may include no target pixel, that is, each pixel unit may be of a three-row or three-column RGB pixel arrangement structure, or of a four-row or four-column RGBW pixel arrangement structure.

Figure 15:
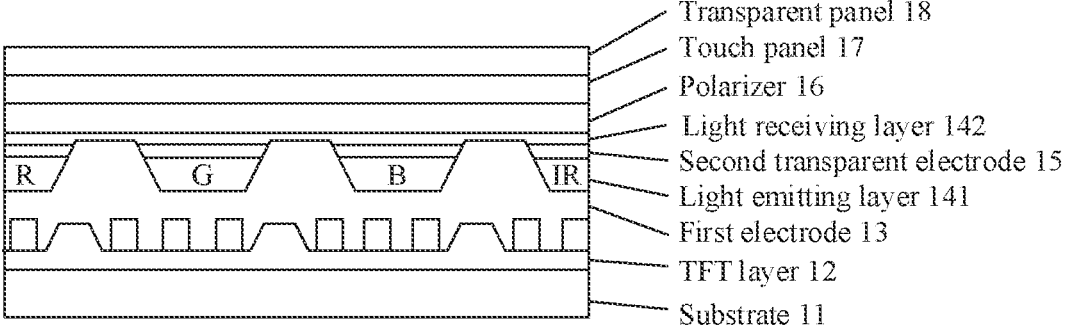
FIG. 15 is a schematic diagram of still another structure of a PPG sensor according to an embodiment of this application.

In another optional implementation, the light receiving layer 142 may be of an integrated structure. FIG. 15 is a schematic diagram of another location of a light receiving pixel according to an embodiment of this application. As shown in FIG. 15, the light receiving layer 142 may be located between the transparent panel 18 and the second transparent electrode 15, to improve a light receiving effect.

A difference between this implementation and the implementation shown in FIG. 14 lies only in that locations of light receiving pixels are different, and other related descriptions are similar. Details are not described herein again.

The light receiving layer 142 may form a relatively large light receiving pixel PD as a whole, to better receive light; or may form a plurality of light receiving pixels PD, to reduce interference between received light with different wavelengths.

(2) A Case in which the PPG Sensor Includes No Display Pixel.

Figure 16:
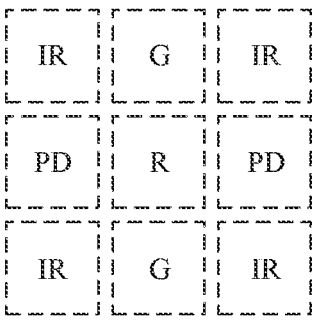
FIG. 16 is a schematic diagram of yet another arrangement structure of pixels according to an embodiment of this application.

Similar to the foregoing implementation, there may be one or more light emitting pixels and one or more light receiving pixels, and the light emitting pixels may relate to a plurality of wavelengths. When there are a plurality of light emitting pixels and a plurality of light receiving pixels, as shown in FIG. 16, the light emitting pixels and the light receiving pixels may form a multi-row and multi-column pixel structure, or may form a honeycomb pixel structure or another pixel structure.

The light emitting pixels and the light receiving pixels may be arranged irregularly or according to a rule, to improve a display effect and a PPG detection effect. For example, the arrangement rule may be that light emitting pixels with various wavelengths and light receiving pixels are alternately arranged, and/or pixels adjacent to the light receiving pixels are light emitting pixels. When the light emitting pixels and the light receiving pixels form the multi-row and multi-column pixel structure, a location relationship between the light emitting pixel and the light receiving pixel is similar to the location relationship between the light emitting pixel and the light receiving pixel in the pixel arrangement structure shown in FIG. 10. Details are not described herein again.

Similar to the implementations shown in FIG. 14 and FIG. 15, the light receiving pixel may also be disposed on an isolation column or a light receiving layer 142 of an integrated structure. Selection may all be performed as required. For related descriptions, refer to FIG. 14 and FIG. 15. Details are not described herein again.

As shown in FIG. 9, in this embodiment, the PPG sensor may further include a TFT layer 12, and the TFT layer 12 may integrate a drive circuit of a light emitting pixel and a receiver circuit of a light receiving pixel. When the display pixel is integrated in the PPG sensor, the TFT layer 12 may further integrate a drive circuit of the display pixel. In this way, assembly costs and a volume of the PPG sensor can be further reduced.

Further, an AFE may be integrated in the TFT layer 12, and the AFE may amplify and sample an optical signal received by the receiver circuit.

In this embodiment of this application, for the PPG sensor, a sensor of a common size may be formed by using an LED as required, or a micro sensor may be formed by using a micro LED and/or a VCSEL (for example, the micro LED is used as a display pixel and the VCSEL is used as a light emitting pixel). Selection may all be specifically performed as required. This is not particularly limited in this embodiment.

In the PPG sensor provided in this embodiment, the substrate, the first electrode, the light emitting layer including the light emitting pixel, the light receiving layer including the light receiving pixel, the second transparent electrode, and the transparent panel may be integrally packaged by using a display packaging process. In this way, assembly costs and a volume of the PPG sensor can be reduced, and a thickness of the PPG sensor and a gap between the PPG sensor and skin can be reduced.

Figure 17:
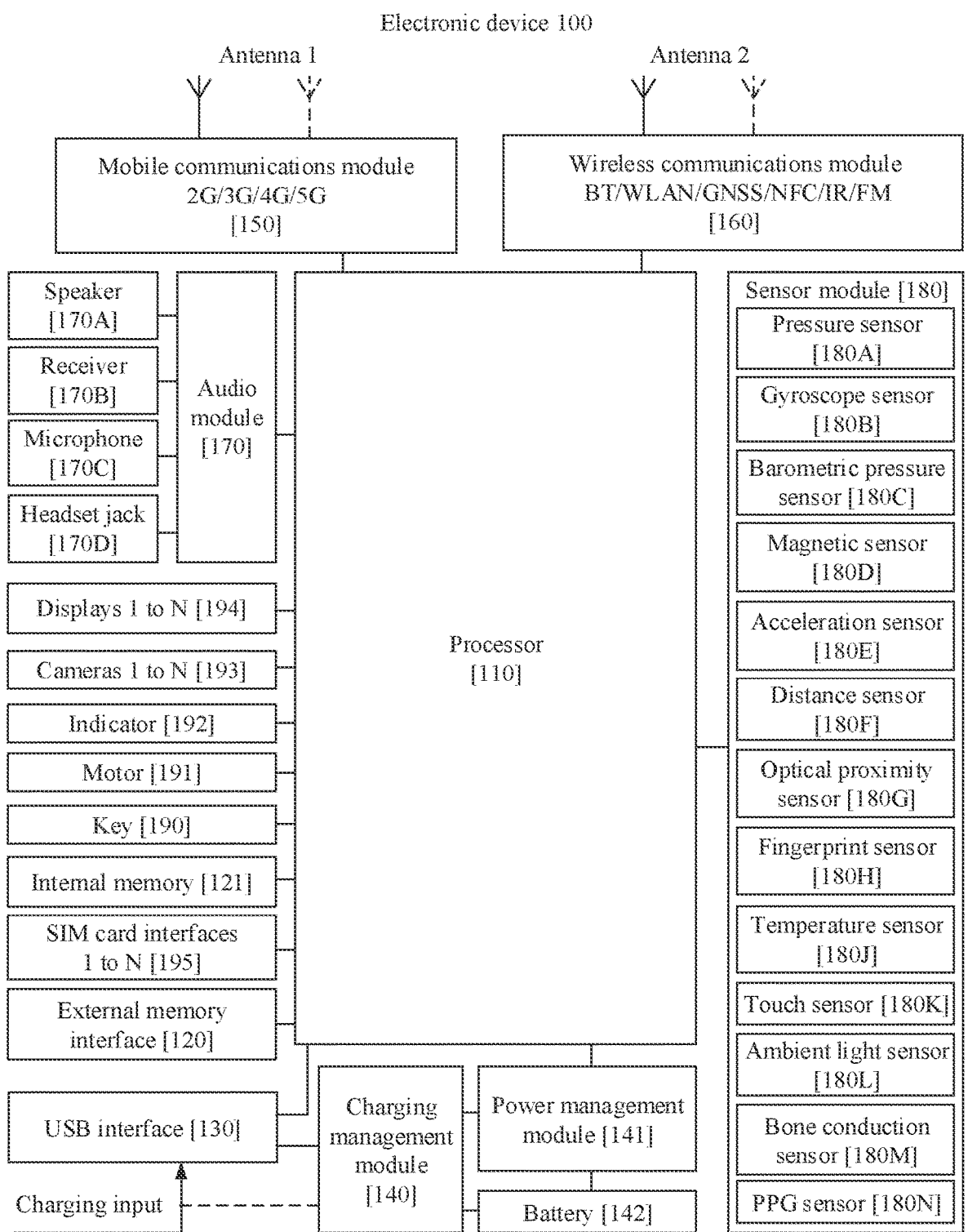
FIG. 17 is a schematic diagram of a structure of an electronic device according to an embodiment of this application.

Based on a same inventive concept, an embodiment of this application further provides an electronic device. FIG. 17 is a schematic diagram of a structure of an electronic device according to an embodiment of this application.

The electronic device 100 may include a processor 110, an external memory interface 120, an internal memory 121, a universal serial bus (USB) interface 130, a charging management module 140, a power management module 141, a battery 142, an antenna 1, an antenna 2, a mobile communications module 150, a wireless communications module 160, an audio module 170, a speaker 170A, a receiver 170B, a microphone 170C, a headset jack 170D, a sensor module 180, a key 190, a motor 191, an indicator 192, a camera 193, a display 194, a subscriber identity module (SIM) card interface 195, and the like. The sensor module 180 may include a pressure sensor 180A, a gyroscope sensor 180B, a barometric pressure sensor 180C, a magnetic sensor 180D, an acceleration sensor 180E, a distance sensor 180F, an optical proximity sensor 180G, a fingerprint sensor 180H, a temperature sensor 180J, a touch sensor 180K, an ambient light sensor 180L, a bone conduction sensor 180M, a PPG sensor 180N, and the like.

It can be understood that the structure shown in this embodiment of the present invention does not constitute a specific limitation on the electronic device 100. In other embodiments of this application, the electronic device 100 may include more or fewer components than those shown in the figure, combine some components, split some components, or have different component arrangements. The components shown in the figure may be implemented by using hardware, software, or a combination of software and hardware.

The processor 110 may control a PPG sensor 180N to work, process a signal collected by the PPG sensor 180N, and implement PPG detection functions such as heart rate detection and blood oxygen detection: and when the PPG sensor 180N integrates display pixels, control the PPG sensor 180N to display an image, a video, and the like, thereby implementing a display function.

The processor 110 may include one or more processing units. For example, the processor 110 may include an application processor (AP), a modem processor, a graphics processing unit (GPU), an image signal processor (ISP), a controller, a memory, a video codec, a digital signal processor (DSP), a baseband processor, a neural-network processing unit (NPU), and/or the like. Different processing units may be independent devices, or may be integrated into one or more processors.

The controller may be a nerve center and a command center of the electronic device 100. The controller may generate an operation control signal based on instruction operation code and a time sequence signal, to complete control of instruction reading and instruction execution.

A memory may be further disposed in the processor 110, and is configured to store instructions and data. In some embodiments, the memory in the processor 110 is a cache. The memory may store instructions or data just used or cyclically used by the processor 110. If the processor 110 needs to use the instructions or the data again, the processor may directly invoke the instructions or the data from the memory. This avoids repeated access and reduces waiting time of the processor 110, thereby improving system efficiency.

In some embodiments, the processor 110 may include one or more interfaces. The interface may include an inter-integrated circuit (I2C) interface, an inter-integrated circuit sound (I2S) interface, a pulse code modulation (PCM) interface, a universal asynchronous receiver/transmitter (UART) interface, a mobile industry processor interface (MIPI), a general-purpose input/output (GPIO) interface, a subscriber identity module (Subscriber Identity Module. SIM) interface, a universal serial bus (USB) interface, and/or the like.

The charging management module 140 is configured to receive a charging input from a charger. The power management module 141 is configured to connect the battery 142 and the charging management module 140 to the processor 110. The power management module 141 receives an input of the battery 142 and/or the charging management module 140, and supplies power to the processor 110, the internal memory 121, an external memory, the display 194, the camera 193, the wireless communications module 160, and the like. The power management module 141 may be further configured to monitor parameters such as a battery capacity, a battery cycle count, and a battery health status (electric leakage or impedance). In some other embodiments, the power management module 141 may alternatively be disposed in the processor 110. In some other embodiments, the power management module 141 and the charging management module 140 may alternatively be disposed in a same device.

A wireless communication function of the electronic device 100 may be implemented through the antenna 1, the antenna 2, the mobile communications module 150, the wireless communications module 160, the modem processor, the baseband processor, and the like.

The antenna 1 and the antenna 2 are configured to: transmit and receive electromagnetic wave signals. Each antenna in the electronic device 100 may be configured to cover one or more communication bands. Different antennas may be further multiplexed, to increase antenna utilization. For example, the antenna 1 may be multiplexed as a diversity antenna in a wireless local area network. In some other embodiments, an antenna may be used in combination with a tuning switch.

The mobile communications module 150 can provide a solution, applied to the electronic device 100, to wireless communication including 2G, 3G, 4G, 5G, and the like. The mobile communications module 150 may include at least one filter, a switch, a power amplifier, a low noise amplifier (LNA), and the like. The mobile communications module 150 may receive an electromagnetic wave through the antenna 1, perform processing such as filtering and amplification on the received electromagnetic wave, and transmit a processed electromagnetic wave to a modem processor for demodulation. The mobile communications module 150 may further amplify a signal modulated by the modem processor, and convert the signal into an electromagnetic wave for radiation through the antenna 1. In some embodiments, at least some function modules of the mobile communications module 150 may be disposed in the processor 110. In some embodiments, at least some function modules of the mobile communications module 150 and at least some modules of the processor 110 may be disposed in a same device.

The wireless communications module 160 may provide wireless communication solutions applied to the electronic device 100, including a wireless local area network (WLAN) (for example, a wireless fidelity (Wi-Fi) network), Bluetooth (BT), a global navigation satellite system (GNSS), frequency modulation (FM), a near field communication (NFC) technology, an infrared (IR) technology, and the like. The wireless communications module 160 may be one or more components integrating at least one communications processing module. The wireless communications module 160 receives an electromagnetic wave through the antenna 2, performs frequency modulation and filtering processing on the electromagnetic wave signal, and sends a processed signal to the processor 110. The wireless communications module 160 may further receive a to-be-sent signal from the processor 110, perform frequency modulation and amplification on the signal, and convert a processed signal into an electromagnetic wave for radiation through the antenna 2.

In some embodiments, in the electronic device 100, the antenna 1 and the mobile communications module 150 are coupled, and the antenna 2 and the wireless communications module 160 are coupled, so that the electronic device 100 can communicate with a network and another device by using a wireless communications technology. The wireless communications technology may include a global system for mobile communications (GSM), a general packet radio service (GPRS), code division multiple access (CDMA), wideband code division multiple access (WCDMA), time division-synchronous code division multiple access (TD-SCDMA), long term evolution (LTE), BT, a GNSS, a WLAN, NFC, FM, and/or an IR technology. The GNSS may include a global positioning system (GPS), a global navigation satellite system (GNSS), and the BeiDou navigation satellite system (BDS), a quasi-zenith satellite system (QZSS), and/or a satellite based augmentation system (SBAS).

The electronic device 100 implements a display function by using the GPU, the display 194, the application processor, and the like. The GPU is a microprocessor for image processing, and is connected to the display 194 and the application processor. The GPU is configured to, perform mathematical and geometric calculation, and render an image. The processor 110 may include one or more GPUs that execute program instructions to generate or change display information.

The display 194 is configured to display an image, a video, and the like. The display 194 includes a display panel. The display panel may use a liquid crystal display (LCD), an organic light-emitting diode (OLED), an active-matrix organic light-emitting diode (AMOLED), a flexible light-emitting diode (FLED), a mini LED, a micro LED, a quantum dot light-emitting diode (QLED), or the like. In some embodiments, the electronic device 100 may include one or N displays 194, where N is a positive integer greater than 1.

The electronic device 100 may implement a photographing function by using the ISP, the camera 193, the video codec, the GPU, the display 194, the application processor, and the like.

The external memory interface 120 may be configured to connect to an external memory card, for example, a micro SD card, to extend a storage capability of the electronic device 100. The external memory card communicates with the processor 110 through the external memory interface 120, to implement a data storage function. For example, files such as music and videos are stored in the external memory card.

The internal memory 121 may be configured to store computer-executable program code. The executable program code includes instructions. The processor 110 runs the instructions stored in the internal memory 121, to implement various function applications and data processing of the electronic device 100. The internal memory 121 may include a program storage area and a data storage area. The program storage area may store an operating system, an application required by at least one function (for example, a voice playing function or an image playing function), and the like. The data storage area may store data (for example, audio data and an address book) and the like created when the electronic device 100 is used. In addition, the internal memory 121 may include a high-speed random access memory, and may further include a non-volatile memory, for example, at least one magnetic disk storage device, a flash storage device, a universal flash storage (UFS), or the like.

The electronic device 100 may implement an audio function such as music playing and recording through the audio module 170, the speaker 170A, the receiver 170B, the microphone 170C, the headset jack 170D, the application processor, and the like.

The PPG sensor 180N may be configured to measure a pulse wave signal. The PPG sensor 180N may be independent of the display, or may be integrated with the display. The application processor may parse heart rate information and blood oxygen information based on the pulse wave signal obtained by the PPG sensor 180N, to implement a heart rate detection function and a blood oxygen detection function. For a specific structure of the PPG sensor 180N, refer to the foregoing embodiments. Details are not described herein again.

In the foregoing embodiments, the description of each embodiment has respective focuses. For a part that is not described in detail or recorded in an embodiment, refer to related descriptions in other embodiments.

In the embodiments provided in this application, it should be understood that the disclosed apparatus/device and method may be implemented in other manners. For example, the described apparatus/device embodiment is merely an example. For example, the division into the modules or the units is merely logical function division and may be other division in actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the apparatuses or units may be implemented in electronic, mechanical, or other forms.

It should be further understood that the term "and/or" used in the specification and claims of this application indicates any combination and all possible combinations of one or more items listed in association, and includes the combinations.

As used in the specification and claims of this application, the term "if" may be interpreted as "when", "once", "in response to determining", or "in response to detecting" depending on the context. Similarly, the phrase "if it is determined" or "if the [described condition or event] is detected" may be interpreted as meaning "once determined" or "in response to determining" or "once the [described condition or event] is detected" or "in response to detecting the [described condition or event]" depending on the context.

In addition, in the descriptions of the specification and claims of this application, the terms "first", "second", "third", and the like are merely intended for a purpose of differentiated description, but shall not be understood as an indication or an implication of relative importance.

Referring to "an embodiment" or "some embodiments" or the like in the specification of this application means that one or more embodiments of this application include a specific feature, structure, or characteristic described with reference to the embodiment. Therefore, statements such as "in an embodiment", "in some embodiments", "in some other embodiments", and "in other embodiments", that appear at different places in this specification do not necessarily mean referring to a same embodiment, but mean "one or more but not all of the embodiments", unless otherwise specifically emphasized. The terms "include", "comprise", "have", and their variants all mean "include but are not limited to", unless otherwise specifically emphasized.

Finally, it should be noted that the foregoing embodiments are merely intended for describing the technical solutions of this application but are not intended to limit this application. Although this application is described in detail with reference to the foregoing embodiments, persons of ordinary skill in the art should understand that they may still make modifications to the technical solutions described in the foregoing embodiments or make equivalent replacements to some or all technical features thereof, without departing from the scope of the technical solutions of the embodiments of this application.

What is claimed is:

1. An electronic device, comprising: a body and a photoplethysmograph (PPG) sensor, wherein the PPG sensor is disposed on the body, and is electrically connected to a circuit board in the body; and the PPG sensor comprises a substrate, a first electrode, a light emitting layer, a light receiving layer, a second transparent electrode, and a transparent panel that are integrally packaged, wherein the substrate and the first electrode are both located on one side of the light emitting layer, and the second transparent electrode and the transparent panel are both located on the other side of the light emitting layer; and the light receiving layer, the first electrode, and the second transparent electrode are located between the substrate and the transparent panel, and a polarity of the first electrode and a polarity of the second transparent electrode are opposite; and the light emitting layer comprises a plurality of light emitting pixels for emitting an optical signal, and the light receiving layer comprises a plurality of light receiving pixels for detecting the optical signal; wherein the light emitting layer further comprises display pixels arranged in an array, and the light emitting layer and the light receiving layer are integrated in a same light emitting-receiving layer.

2. The electronic device according to claim 1, wherein the light emitting layer comprises a central region and an edge region around the central region, the display pixels are distributed in the central region, and at least one of the plurality of the light emitting pixels and at least one of the plurality of the light receiving pixels are distributed in the edge region.

3. The electronic device according to claim 1, wherein the display pixels comprise a first display pixel, a second display pixel, and a third display pixel in different colors, and three colors of the first display pixel, the second display pixel, and the third display pixel are respectively red, green, and blue; and the first display pixel and target pixels are alternately arranged in a first direction, the first display pixel and the second display pixel are alternately arranged in a second direction, the second display pixel and the third display pixel are alternately arranged in the first direction, and the first direction is perpendicular to the second direction; and and the target pixels comprise more than one of the light emitting pixels and more than one of the light receiving pixels.

4. The electronic device according to claim 3, wherein the plurality of light emitting pixels relate to a plurality of wavelengths, the target pixels comprise the plurality of the light emitting pixels and the plurality of light receiving pixels, and each target pixel adjacent to one of the plurality of light receiving pixels is one of the plurality of light emitting pixels.

5. The electronic device according to claim 4, wherein for each light receiving pixel, light emitting pixels adjacent to the light receiving pixel comprise a red light emitting pixel and an infrared light emitting pixel, a distance between the red light emitting pixel and the light receiving pixel is equal to a distance between the infrared light emitting pixel and the light receiving pixel.

6. The electronic device according to claim 5, wherein the light emitting pixels comprise a first light emitting pixel, a second light emitting pixel, and a green light emitting pixel, one of the first light emitting pixel and the second light emitting pixel is the red light emitting pixel, and the other is the infrared light emitting pixel; and the first light emitting pixel and the green light emitting pixel are alternately arranged in the first direction, the first light emitting pixel and the light receiving pixel are alternately arranged in the second direction, and the light receiving pixel and the second light emitting pixel are alternately arranged in the first direction.

7. The electronic device according to claim 3, wherein the light emitting pixels comprise more than one red display pixels or more than one green display pixels among the display pixels, and the target pixels comprise the light receiving pixels.

8. The electronic device according to claim 7, wherein the light emitting pixels further comprise infrared light emitting pixels, and the target pixels further comprise the infrared light emitting pixels; and at least one of the following is true:

each target pixel adjacent to one of the light receiving pixels is one of the infrared light emitting pixels, or each target pixel adjacent to one of the infrared light emitting pixels is one of the light receiving pixels.

9. The electronic device according to claim 3, wherein each display pixel comprises four subpixels in corresponding colors.

10. The electronic device according to claim 1, wherein the display pixels comprise red display pixels, green display pixels, and blue display pixels, the light emitting layer comprises pixel units arranged in an array, each pixel unit comprises one red display pixel, one green display pixel, one blue display pixel, and one target pixel that are sequentially arranged in a first direction, and the target pixels comprise more than one of the light emitting pixels.

11. The electronic device according to claim 10, wherein the light emitting pixels comprise an infrared light emitting pixel, a red light emitting pixel, and a green light emitting pixel, and the target pixels comprise the plurality of light emitting pixels; or the light emitting pixels comprise more than one red display pixels and more than one green display pixels among the display pixels, and an infrared light emitting pixel, and the target pixels comprise the infrared light emitting pixel.

12. The electronic device according to claim 11, wherein the target pixels further comprise at least one of the plurality of the light receiving pixels.

13. The electronic device according to claim 11, wherein there is an isolation column between the display pixel and each adjacent pixel among the target pixels, at least one of the plurality of the light receiving pixels is disposed on the isolation column.

14. The electronic device according to claim 1, wherein a light source of the display pixels is a miniature light-emitting diode (LED), and a light source of at least one of the plurality of the light emitting pixels is a miniature LED or a vertical-cavity surface-emitting laser (VCSEL).

15. The electronic device according to claim 1, wherein the light emitting pixels relate to a plurality of wavelengths, and the light emitting pixels with various wavelengths and the light receiving pixels are alternately arranged.

16. The electronic device according to claim 15, wherein each pixel adjacent to one of the plurality of light receiving pixels is a light emitting pixel.

17. The electronic device according to claim 1, wherein the light receiving layer is located between the second transparent electrode and the transparent panel.

18. The electronic device according to claim 1, wherein the electronic device further comprises a thin film transistor (TFT) layer located between the substrate and the first electrode, and a drive circuit of at least one of the plurality of the light emitting pixels and a receiver circuit of at least one of the plurality of the light receiving pixels are integrated in the TFT layer.

19. The electronic device according to claim 18, wherein an analog front end (AFE) circuit is integrated in the TFT layer, and the AFE is configured to amplify and sample an optical signal received by the receiver circuit.

20. The electronic device according to claim 1, wherein the PPG sensor further comprises at least one of a polarizer or a touch panel that is located between the second transparent electrode and the transparent panel.

* * * * *